US010265259B2

(12) United States Patent
Schroeder et al.

(10) Patent No.: US 10,265,259 B2
(45) Date of Patent: Apr. 23, 2019

(54) CONDITIONING HAIR-CLEANING AGENT

(71) Applicant: Henkel AG & Co. KGaA, Duesseldorf (DE)

(72) Inventors: Thomas Schroeder, Hamburg (DE); Dirk Hentrich, Hamburg (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 14/454,580

(22) Filed: Aug. 7, 2014

(65) Prior Publication Data

US 2014/0348927 A1 Nov. 27, 2014

Related U.S. Application Data

(63) Continuation of application No. PCT/EP2013/051733, filed on Jan. 30, 2013.

(30) Foreign Application Priority Data

Feb. 8, 2012 (DE) .................. 10 2012 201 861

(51) Int. Cl.
| | |
|---|---|
| A61K 8/58 | (2006.01) |
| A61Q 5/02 | (2006.01) |
| A61Q 5/12 | (2006.01) |
| A61K 8/73 | (2006.01) |
| A61K 8/891 | (2006.01) |
| A61K 8/92 | (2006.01) |
| A61K 8/42 | (2006.01) |
| A61Q 5/00 | (2006.01) |

(52) U.S. Cl.
CPC ............... *A61K 8/585* (2013.01); *A61K 8/42* (2013.01); *A61K 8/58* (2013.01); *A61K 8/73* (2013.01); *A61K 8/731* (2013.01); *A61K 8/737* (2013.01); *A61K 8/891* (2013.01); *A61K 8/92* (2013.01); *A61K 8/922* (2013.01); *A61Q 5/006* (2013.01); *A61Q 5/02* (2013.01); *A61Q 5/12* (2013.01); *A61K 2800/596* (2013.01)

(58) Field of Classification Search
None
See application file for complete search history.

(56) References Cited

U.S. PATENT DOCUMENTS

| | | | | |
|---|---|---|---|---|
| 7,347,993 B2* | 3/2008 | Bracken | ............... | A61K 8/891 424/70.12 |
| 7,674,848 B2* | 3/2010 | Lin | .................. | A01N 25/04 524/313 |
| 2006/0293197 A1 | 12/2006 | Uehara et al. | | |
| 2011/0124542 A1 | 5/2011 | Sartingen | | |

FOREIGN PATENT DOCUMENTS

| | | | |
|---|---|---|---|
| DE | 19710873 A1 | 9/1998 | |
| EP | 0337354 A1 | 10/1989 | |
| EP | 0398177 A2 | 11/1990 | |
| EP | 0432951 A2 | 6/1991 | |
| EP | 0468721 A1 * | 7/1991 | |
| EP | 0468721 A1 * | 1/1992 | ............. A61K 8/068 |
| EP | 0468721 A1 * | 1/1992 | ............. A61K 8/068 |
| EP | 0529883 A1 | 3/1993 | |
| EP | 0674898 B2 | 10/1995 | |
| EP | 1702974 A1 | 9/2006 | |
| EP | 1977728 A2 | 10/2008 | |
| WO | 97/35548 A1 | 10/1997 | |
| WO | 00/45779 A1 | 8/2000 | |
| WO | 0243671 A2 | 6/2002 | |
| WO | 03028683 A1 | 4/2003 | |
| WO | 03047544 A1 | 6/2003 | |
| WO | 2004/026270 A1 | 4/2004 | |
| WO | 2005000257 A1 | 1/2005 | |
| WO | 2005046628 A1 | 5/2005 | |
| WO | 2007042085 A1 | 4/2007 | |
| WO | 2008055816 A1 | 5/2008 | |
| WO | 2009/153280 A1 | 12/2009 | |

OTHER PUBLICATIONS

Summers (Hair Care Basics, published online Jun. 19, 2009).*
Real Health Hair Center, Why having the proper pH is your hairs best friend, Nov. 1, 2011.*
Real Health Hair Center, Why having the proper pH is your hairs best friend, Nov. 1, 2011 (Year: 2011).*
Summers (Hair Care Basics, published online Jun. 19, 2009). (Year: 2009).*
PCT International Search Report (PCT/EP2013/051733) dated Nov. 14, 2013.
"Orange Peel Wax # 139". KosterKeunen, www.koster-wax.com/us/wax-products/flower-waxes/orange-peel-wax--139. Accessed May 24, 2017 (in Beiersdorf AG Opposition of Patent Application EP 2 812 076).
"1785 Emulsion". Dow Corning, Jan. 14, 2003. pp. 1-4. Ref No. 27-1065-01.
"HMW 2220 Non-Ionic Emulsion". Dow Corning, www.dowcorning.com/content/publishedlit/DC%28R%29HMW2220NonIonicEmulsion.pdf. Mar. 25, 2009. Ref No. 22-1846I-01.
"Mackester EGDS". Rhodia, www.glenncorp.com/wp-content/uploads/2013/08/Mackester-EGDS1.pdf. Jan. 2010. pp. 1-2.
"Thixcin R". Elementis Specialities, www.elementisspecialties.com/esweb/webproducts.nsf/allbydocid/FD45CA269A2340DE852575F90060132D/$FI LE/PDS-TH IXCI N%C2%AE%20R.pdf. Nov. 30, 2016.

(Continued)

*Primary Examiner* — Robert A Wax
*Assistant Examiner* — Melissa S Mercier
(74) *Attorney, Agent, or Firm* — James J. Cummings

(57) ABSTRACT

Cosmetic cleaning agents include in a cosmetically acceptable carrier a) at least one anionic surfactant, b) at least one cationic guar polymer, c) at least one silicone emulsion, in which the silicone particles have an average diameter of a maximum of 600 nm, and d) at least one wax. The cosmetic cleaning agents are suitable in particular for use as a shampoo. After application they impart improved properties to the hair treated therewith, in particular improved wet and dry combability.

9 Claims, No Drawings

(56) References Cited

OTHER PUBLICATIONS

Opposition Notice EP 2 812 076 (Appln No. 13 701 781.0) Opponent: Beiersdorf AG Date Submitted: May 24, 2017 21 pages.
Opposition Notice EP 2 812 076 (Appln No. 13 701 781.0) Opponent: The Procter & Gamble Company Date Submitted: May 30, 2017 18 pages.
Opposition Notice EP 2 812 076 (Appln No. 13 701 781.0) Opponent: L'OREAL Date Submitted: May 31, 2017 4 pages.

* cited by examiner

CONDITIONING HAIR-CLEANING AGENT

FIELD OF THE INVENTION

The present invention generally relates to cosmetics, and more particularly relates to cleaning agents that include in a cosmetically acceptable carrier an anionic surfactant, a cationic guar polymer, a silicone emulsion and a wax.

BACKGROUND OF THE INVENTION

Cosmetic cleaning agents, such as hair shampoos, are based on conventional anionic, amphoteric, zwitterionic, non-ionic and/or cationic surfactants. Owing to their outstanding cleaning and foaming ability, anionic surfactants, optionally mixed with small amounts of co-surfactants, are predominantly used.

Such a commercial shampoo cleans the hair and removes sebaceous residues and/or residues of styling agents and other impurities from the surface of the hair and from the scalp. However, the cleaning process also removes lipids and proteins from the hair and scalp, which can damage the hair structure and cause the scalp to dry out, particularly with frequent cleaning.

To eliminate these disadvantages, many cosmetic cleaning agents additionally include care substances such as for example vegetable oils, silicones or special polymers.

In many cases, however, care substances based on oils, fats and/or waxes have a disadvantageous effect on the foam properties and storage stability of the cleaning agents, as a result of which in the past either additional (polymeric) stabilizing agents and/or larger amounts of surfactants were used.

Document WO 97/35548A1 for example discloses conditioning hair shampoos that include a mixture of anionic and amphoteric surfactants, a silicone emulsion and a cationic polymer. The shampoos include either larger amounts of surfactants or additional stabilizing agents (carbopols).

For environmental reasons the manufacturers of cosmetic cleaning agents have tried in recent years to increase the efficiency of the agents without using larger amounts of surfactants or additional stabilizing agents (more optimum use of resources).

It is therefore desirable to provide caring cleaning agents having good foam properties.

The use of larger amounts of surfactants and/or additional stabilizing agents should be avoided as far as possible, without reducing the effectiveness of the agents.

The cleaning agents should be suitable in particular for the gentle cleaning and care of the hair, and after application they should impart an improved combability and improved visual and tactile properties to the hair.

Furthermore, other desirable features and characteristics of the present invention will become apparent from the subsequent detailed description of the invention and the appended claims, taken in conjunction with the accompanying drawings and this background of the invention.

Brief Summary of the Invention

It was found that cleaning agents based on anionic surfactants, special cationic polymers, waxes and silicones are outstandingly suitable for the purposes set forth above. The corresponding cleaning agents care for and clean the hair and in combination with water form a creamy, fine-pored foam.

According to the present invention, a cosmetic cleaning agent includes in a cosmetically acceptable carrier, at least one anionic surfactant, at least one cationic guar polymer, at least one silicone emulsion, in which the silicone particles have an average diameter of a maximum of 600 nm, and at least one wax.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The invention firstly provides a cosmetic cleaning agent that includes in a cosmetically acceptable carrier
a) at least one anionic surfactant,
b) at least one cationic guar polymer,
c) at least one silicone emulsion, in which the silicone particles have an average diameter of a maximum of 600 nm, and
d) at least one wax.

The compositions according to the invention include components a) to d) in a cosmetically acceptable carrier. This is preferably aqueous or aqueous-alcoholic. The cosmetic carrier preferably includes at least 50 wt. %, more preferably at least 60 wt. % and particularly preferably at least 70 wt. % water.

The cosmetic carrier can moreover include 0.01 to 50 wt. %, preferably 0.05 to 40 wt. % and in particular 0.1 to 30 wt. % of at least one alcohol, which can be selected from ethanol, ethyl diglycol, 1-propanol, 2-propanol, isopropanol, 1,2-propylene glycol, glycerol, diglycerol, triglycerol, 1-butanol, 2-butanol, 1,2-butanediol, 1,3-butanediol, 1-pentanol, 2-pentanol, 1,2-pentanediol, 1,5-pentanediol, 1-hexanol, 2-hexanol, 1,2-hexanediol, 1,6-hexanediol, polyethylene glycols, sorbitol, sorbitan, benzyl alcohol, phenoxyethanol or mixtures of said alcohols.

The water-soluble alcohols are preferred.

Ethanol, ethyl diglycol, 1-propanol, 2-propanol, isopropanol, 1,2-propylene glycol, glycerol, benzyl alcohol and/or phenoxyethanol and mixtures of said alcohols are preferred in particular.

The suitable anionic surfactants a), which can be used in the agents according to the invention, include for example:
- linear and branched fatty acids having 8 to 30 C atoms (soaps),
- ether carboxylic acids of the formula R—O—($CH_2$—$CH_2O)_x$—$CH_2$—COOH, in which R is a linear or branched, saturated or unsaturated alkyl group having 8 to 30 C atoms and x=0 or 1 to 16,
- acyl sarcosides having 8 to 24 C atoms in the acyl group,
- acyl taurides having 8 to 24 C atoms in the acyl group,
- acyl isethionates having 8 to 24 C atoms in the acyl group,
- sulfosuccinic acid mono- and/or dialkyl esters having 8 to 24 C atoms in the alkyl group and sulfosuccinic acid monoalkyl polyoxyethyl esters having 8 to 24 C atoms in the alkyl group and 1 to 6 oxyethyl groups,
- alpha-olefin sulfonates having 8 to 24 C atoms,
- alkyl sulfate and/or alkyl polyglycol ether sulfate salts of formula R—($OCH_2$—$CH_2)_x$—$OSO_3^-$ $X^+$, in which R preferably denotes a linear or branched, saturated or unsaturated alkyl group having 8 to 30 C atoms, x denotes the number 0 or 1 to 12 and X denotes an alkali, alkaline-earth, ammonium or alkanolamine ion, sulfonates of unsaturated fatty acids having 8 to 24 C atoms and 1 to 6 double bonds,
esters of tartaric acid and citric acid with alcohols that are addition products of approximately 2 to 15 molecules of ethylene oxide and/or propylene oxide with fatty alcohols having 8 to 22 C atoms,
alkyl and/or alkenyl ether phosphates of the formula

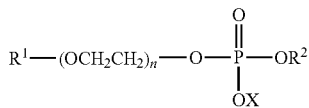

in which $R^1$ preferably denotes an aliphatic hydrocarbon residue having 8 to 30 carbon atoms, $R^2$ denotes hydrogen, a $(CH_2CH_2O)_nR^1$ residue or X, n denotes numbers from 0 to 10 and X denotes hydrogen, an alkali or alkaline-earth metal or the $NR^3R^4R^5R^6$ group, with $R^3$ to $R^6$ independently of one another denoting a $C_1$ to $C_4$ hydrocarbon residue.

Preferred anionic surfactants are alkyl sulfate and/or alkyl polyglycol ether sulfate salts of formula $R-(OCH_2-CH_2)_x-OSO_3^-X^+$, in which R preferably denotes a linear or branched, saturated or unsaturated alkyl group having 8 to 30 C atoms, x denotes the number 0 or 1 to 12 and X denotes an alkali, alkaline-earth, ammonium or alkanolamine ion.

Particularly preferred anionic surfactants are straight-chain or branched alkyl ether sulfates of the aforementioned formula, including an alkyl residue having 8 to 18 and in particular 10 to 16 C atoms along with 1 to 6 and in particular 2 to 4 ethylene oxide units.

The sodium, magnesium and/or triethanolamine salts of linear or branched lauryl, tridecyl and/or myristyl sulfates having a degree of ethoxylation of 2 to 4 are preferred in particular.

The anionic surfactant(s) is (are) used in the cleaning agents according to the invention—relative to their total weight—in an amount preferably from 6 to 12 wt. %, more preferably from 7 to 11 wt. % and in particular from 8 to 10 wt. %.

In the context of the present invention suitable cationic guar polymers b) are understood to be physiologically acceptable cationic guar derivatives and/or hydrophobically modified cationic guar derivatives.

Cationic hydroxy($C_1$-$C_4$)alkyl guar derivatives, preferably cationic hydroxyethyl trimethylammonium guar and/or cationic hydroxypropyl trimethylammonium guar, having average molecular weights (weight-average) from 100,000 to 2,000,000 daltons, preferably from 400,000 to 1,750,000 daltons and in particular from 800,000 to 1,600,000 daltons, are preferred.

Also preferred are cationic hydroxy($C_1$-$C_4$)alkyl guar derivatives, preferably cationic hydroxyethyl trimethylammonium guar and/or cationic hydroxypropyl trimethylammonium guar, with cationic charge densities of at least 0.5 meq/g.

Preferred in particular are the cationic guar polymers known under the INCI name Guar Hydroxypropyltrimonium Chloride and having a molecular weight (weight-average) from 100,000 to 2,000,000 daltons, preferably from 400,000 to 1,750,000 daltons and in particular from 800,000 to 1,600,000 daltons and a cationic charge density of at least 0.5 meq/g.

Suitable cationic guar polymers b) are available from various suppliers under the trade names "Jaguar®" or "N-Hance®", for example.

Particularly suitable cationic guar polymers b) are: Jaguar® C13S, Jaguar® Excel, N-Hance® 3196 and/or N-Hance® 3215.

The cosmetic cleaning agents preferably include the cationic polymer(s) b) in an amount from 0.01 to 1 wt. %, more preferably from 0.025 to 0.75 wt. % and in particular from 0.05 to 0.5 wt. %, the stated amounts relating to the total weight of the cleaning agents.

The cleaning agents according to the invention include as conditioning agents at least one silicone emulsion, in which the silicone particles have an average diameter of a maximum of 600 nm.

Such emulsions are commercially available from various suppliers.

Their use in the cleaning agents according to the invention has the advantage that the fine silicone particles can be deposited particularly well on the hair surface without weighing down the hair.

Within the meaning of the present invention the "average diameter of the silicone particles" is preferably understood to be the volume-average silicone particle diameter D50, which can be determined by the conventional methods, for example by laser diffractometry.

The volume-average particle diameter D50 is the point in the particle size distribution at which 50 vol. % of the silicone particles have a smaller diameter and 50 vol. % of the silicone particles have a larger diameter.

Suitable silicones that can be included in the silicone emulsions c) can be selected from:
(i) polyalkylsiloxanes, polyarylsiloxanes, polyalkylarylsiloxanes, which can be volatile or non-volatile, straight-chain, branched or cyclic, crosslinked or uncrosslinked;
(ii) polysiloxanes which in their general structure include one or more organo functional groups, which can be selected from:
 a) substituted or unsubstituted aminated groups;
 b) (per)fluorinated groups;
 c) thiol groups;
 d) carboxylate groups;
 e) hydroxylated groups;
 f) alkoxylated groups;
 g) acyloxyalkyl groups;
 h) amphoteric groups;
 i) bisulfite groups;
 j) hydroxyacyl amino groups;
 k) carboxyl groups
 l) sulfonic acid groups; and
 m) sulfate or thiosulfate groups;
(iii) linear polysiloxane(A)-polyoxyalkylene(B) block copolymers of the type $(A-B)_n$, where n>3;
(iv) grafted silicone polymers having a non-silicone-containing, organic framework consisting of an organic main chain formed from organic monomers containing no silicone, onto which at least one polysiloxane macromer has been grafted in the chain and optionally on at least one chain end;
(v) grafted silicone polymers having a polysiloxane framework, onto which non-silicone-containing, organic monomers have been grafted, which have a polysiloxane main chain onto which at least one organic macromer containing no silicone has been grafted in the chain and optionally on at least one of its ends;
(vi) or mixtures thereof.

Preferred silicone emulsions include non-volatile polyalkyl siloxanes, preferably polydialkyl siloxanes, with methyl groups in particular being understood to be preferred alkyl groups.

Further preferred silicone emulsions include as the silicone polydimethyl siloxane, which at a temperature of 25° C. preferably has a viscosity in the range from 1000 to 1,000,000 cSt, more preferably from 5000 to 500,000 cSt, particularly preferably from 10,000 to 200,000 cSt and in particular from 30,000 to 100,000 cSt.

The viscosity of the polysiloxanes can be measured for example at 25° C. using a glass capillary viscometer in accordance with the Dow Corning corporate test method CTM0004 (Jul. 20, 1970).

Particularly suitable silicone emulsions are for example those which preferably include (i) 20 to 80 wt. %, more preferably 30 to 70 wt. % and in particular 40 to 60 wt. % of at least one polydialkyl siloxane—preferably a previously defined polydimethyl siloxane—and
(ii) at least two different non-ionic emulsifiers, which are selected from in each case one of the two groups of 1- to 5-times alkoxylated $C_8$-$C_{24}$ alcohols and 18- to 30-times alkoxylated $C_8$-$C_{24}$ alcohols, the stated amounts relating to the weight of the silicone emulsions.

Particularly preferred non-ionic emulsifiers which can be used in the silicone emulsions c) that are suitable according to the invention are ethoxylated lauryl alcohols. The ethoxylated fatty alcohols known under the INCI names Laureth-4 and Laureth-23 are preferred in particular.

One example of a commercially available silicone emulsion which can preferably be used in the cleaning agents according to the invention is Xiameter® MEM 1664 (formerly Dow Corning® 1664 Emulsion) from Dow Corning.

The silicone emulsion c) is preferably used in the cleaning agents according to the invention in an amount from 0.05 to 2 wt. %, more preferably from 0.1 to 1.5 wt. % and in particular from 0.2 to 1 wt. %, the stated amounts relating to the total weight of the cleaning agents.

Within the context of the invention suitable "waxes" (d)) are understood to be natural and synthetic substances which usually have the following properties: kneadable at 20° C., solid to crumbly, coarsely to finely crystalline, translucent to opaque, but not glassy, melting above 40° C. without decomposing, relatively low in viscosity and not ropy even just above the melting point, highly temperature-dependent consistency and solubility, polishable under light pressure.

Natural waxes are understood to be preferably plant waxes such as carnauba wax, candelilla wax and/or jojoba oil as well as animal waxes such as beeswax, wool wax, spermaceti wax and/or uropygial gland oil.

Synthetic waxes are understood to be preferably mineral waxes such as hard paraffin, ceresin, ozocerite, ester waxes such as polyethylene glycol or polyethylene glycol ester waxes and/or hydrogenated vegetable oils.

The cleaning agents according to the invention preferably include at least one chemically modified (in particular hydrogenated) or unmodified wax of plant origin, which preferably has a melting point in the range from 80 to 90° C., more preferably from 82 to 90° C. and in particular from 85 to 88° C.

The cleaning agents according to the invention particularly preferably include at least one hydrogenated vegetable oil, in particular preferably hydrogenated castor oil.

The wax(es) can preferably be included in the cleaning agents according to the invention in an amount from 0.02 to 1 wt. %, more preferably from 0.03 to 0.75 wt. % and in particular from 0.05 to 0.5 wt. %, the stated amounts relating to the total weight of the cleaning agents.

In a first preferred embodiment cleaning agents according to the invention include—relative in each case to their total weight— a) 6 to 12 wt. %, preferably 7 to 11 wt. % and in particular 8 to 10 wt. % of at least one anionic surfactant,
b) 0.01 to 1 wt. %, preferably 0.025 to 0.75 wt. % and in particular 0.05 to 0.5 wt. % of at least one cationic guar polymer,
c) 0.05 to 2 wt. %, preferably 0.1 to 1.5 wt. % and in particular 0.2 to 1 wt. % of at least one silicone emulsion, which has an average silicone particle size by volume of a maximum of 600 nm, and
d) 0.02 to 1 wt. %, preferably 0.03 to 0.75 wt. % and in particular 0.05 to 0.5 wt. % of at least one wax.

Within this embodiment it is particularly preferable if the cleaning agents according to the invention include—relative in each case to their total weight— a) 6 to 12 wt. %, preferably 7 to 11 wt. % and in particular 8 to 10 wt. % of at least one alkyl sulfate and/or alkyl polyglycol ether sulfate salt of formula R—(OCH$_2$—CH$_2$)$_x$—OSO$_3^-$ X$^+$, in which R preferably denotes a linear or branched, saturated or unsaturated alkyl group having 8 to 30 C atoms, x denotes the number 0 or 1 to 12 and X denotes an alkali, alkaline-earth, ammonium or alkanolamine ion,
b) 0.01 to 1 wt. %, preferably 0.025 to 0.75 wt. % and in particular 0.05 to 0.5 wt. % of at least one cationic hydroxy($C_1$-$C_4$)alkyl guar derivative having an average molecular weight (weight-average) from 100,000 to 2,000,000 daltons, preferably from 400,000 to 1,750,000 daltons and in particular from 800,000 to 1,600,000 daltons,
c) 0.05 to 2 wt. %, preferably 0.1 to 1.5 wt. % and in particular 0.2 to 1 wt. % of at least one dimethyl polysiloxane emulsion, which has an average silicone particle size by volume of a maximum of 600 nm, and
d) 0.02 to 1 wt. %, preferably 0.03 to 0.75 wt. % and in particular 0.05 to 0.5 wt. % of at least one wax of plant origin, which preferably has a melting point in the range from 80 to 90° C.

Cleaning agents that are preferred in particular within this first preferred embodiment include—relative to the total weight of the cleaning agents— a) 6 to 12 wt. %, preferably 7 to 11 wt. % and in particular 8 to 10 wt. % of at least one straight-chain or branched alkyl ether sulfate of the above formula, which has an alkyl residue having 8 to 18 and in particular 10 to 16 C atoms and 1 to 6 and in particular 2 to 4 ethylene oxide units, 0.01 to 1 wt. %, preferably 0.025 to 0.75 wt. % and in particular 0.05 to 0.5 wt. % of at least one cationic guar polymer known under the INCI name Guar Hydroxypropyltrimonium Chloride and having a molecular weight (weight-average) from 100,000 to 2,000,000 daltons, preferably from 400,000 to 1,750,000 daltons and in particular from 800,000 to 1,600,000 daltons and a cationic charge density of at least 0.5 meq/g,
c) 0.05 to 2 wt. %, preferably 0.1 to 1.5 wt. % and in particular 0.2 to 1 wt. % of at least one dimethyl polysiloxane emulsion, which has an average silicone particle size by volume of a maximum of 600 nm, and
d) 0.02 to 1 wt. %, preferably 0.03 to 0.75 wt. % and in particular 0.05 to 0.5 wt. % of at least one hydrogenated vegetable oil, preferably hydrogenated castor oil.

To increase the hair-conditioning properties, cleaning agents according to the invention can additionally include in a further preferred embodiment 0.01 to 1 wt. %, preferably 0.025 to 0.75 wt. % and in particular 0.05 to 0.5 wt. % of at least one vegetable oil.

Within the context of the present invention suitable vegetable (natural, native) oils are understood to be preferably triglycerides and mixtures of triglycerides. Preferred natural oils are coconut oil, (sweet) almond oil, walnut oil, peach kernel oil, apricot kernel oil, avocado oil, tea tree oil, soybean oil, sesame oil, sunflower oil, tsubaki oil, evening primrose oil, rice bran oil, palm kernel oil, mango kernel oil, lady's smock oil, thistle oil, macadamia nut oil, grape seed oil, amaranth seed oil, argan oil, bamboo oil, olive oil, wheatgerm oil, pumpkin seed oil, mallow oil, hazelnut oil, safflower oil, canola oil, sasanqua oil, jojoba oil, rambutan oil, cocoa butter, shea butter and/or mixtures of these oils.

In a second preferred embodiment cleaning agents according to the invention therefore include—relative in each case to their total weight—
a) 6 to 12 wt. %, preferably 7 to 11 wt. % and in particular 8 to 10 wt. % of at least one anionic surfactant,
b) 0.01 to 1 wt. %, preferably 0.025 to 0.75 wt. % and in particular 0.05 to 0.5 wt. % of at least one cationic guar polymer,
c) 0.05 to 2 wt. %, preferably 0.1 to 1.5 wt. % and in particular 0.2 to 1 wt. % of at least one silicone emulsion, which has an average silicone particle size by volume of a maximum of 600 nm,
d) 0.02 to 1 wt. %, preferably 0.03 to 0.75 wt. % and in particular 0.05 to 0.5 wt. % of at least one wax, and
e) 0.01 to 1 wt. %, preferably 0.025 to 0.75 wt. % and in particular 0.05 to 0.5 wt. % of at least one vegetable oil.

Within this embodiment it is particularly preferable if the cleaning agents according to the invention include—relative in each case to their total weight—
a) 6 to 12 wt. %, preferably 7 to 11 wt. % and in particular 8 to 10 wt. % of at least one alkyl sulfate and/or alkyl polyglycol ether sulfate salt of formula R—(OCH$_2$—CH$_2$)$_x$—OSO$_3^-$ X$^+$, in which R preferably denotes a linear or branched, saturated or unsaturated alkyl group having 8 to 30 C atoms, x denotes the number 0 or 1 to 12 and X denotes an alkali, alkaline-earth, ammonium or alkanolamine ion,
b) 0.01 to 1 wt. %, preferably 0.025 to 0.75 wt. % and in particular 0.05 to 0.5 wt. % of at least one cationic hydroxy(C$_1$-C$_4$)alkyl guar derivative having an average molecular weight (weight-average) from 100,000 to 2,000,000 daltons, preferably from 400,000 to 1,750,000 daltons and in particular from 800,000 to 1,600,000 daltons,
c) 0.05 to 2 wt. %, preferably 0.1 to 1.5 wt. % and in particular 0.2 to 1 wt. % of at least one dimethyl polysiloxane emulsion, which has an average silicone particle size by volume of a maximum of 600 nm,
d) 0.02 to 1 wt. %, preferably 0.03 to 0.75 wt. % and in particular 0.05 to 0.5 wt. % of at least one wax of plant origin, which preferably has a melting point in the range from 80 to 90° C., and
e) 0.01 to 1 wt. %, preferably 0.025 to 0.75 wt % and in particular 0.05 to 0.5 wt. % of at least one vegetable oil, selected from coconut oil, (sweet) almond oil, walnut oil, peach kernel oil, apricot kernel oil, avocado oil, tea tree oil, soybean oil, sesame oil, sunflower oil, tsubaki oil, evening primrose oil, rice bran oil, palm kernel oil, mango kernel oil, lady's smock oil, thistle oil, macadamia nut oil, grape seed oil, amaranth seed oil, argan oil, bamboo oil, olive oil, wheatgerm oil, pumpkin seed oil, mallow oil, hazelnut oil, safflower oil, canola oil, sasanqua oil, jojoba oil, rambutan oil, cocoa butter, shea butter and/or mixtures of these oils.

Cleaning agents that are preferred in particular within this second preferred embodiment include—relative to the total weight of the cleaning agents—
a) 6 to 12 wt. %, preferably 7 to 11 wt. % and in particular 8 to 10 wt. % of at least one straight-chain or branched alkyl ether sulfate of the above formula, which has an alkyl residue having 8 to 18 and in particular 10 to 16 C atoms and 1 to 6 and in particular 2 to 4 ethylene oxide units,
b) 0.01 to 1 wt. %, preferably 0.025 to 0.75 wt. % and in particular 0.05 to 0.5 wt. % of at least one cationic guar polymer known under the INCI name Guar Hydroxypropyltrimonium Chloride and having a molecular weight (weight-average) from 100,000 to 2,000,000 daltons, preferably from 400,000 to 1,750,000 daltons and in particular from 800,000 to 1,600,000 daltons and a cationic charge density of at least 0.5 meq/g,
c) 0.05 to 2 wt. %, preferably 0.1 to 1.5 wt. % and in particular 0.2 to 1 wt. % of at least one dimethyl polysiloxane emulsion, which has an average silicone particle size by volume of a maximum of 600 nm,
d) 0.02 to 1 wt. %, preferably 0.03 to 0.75 wt. % and in particular 0.05 to 0.5 wt. % of at least one hydrogenated vegetable oil, preferably hydrogenated castor oil, and
e) 0.01 to 1 wt. %, preferably 0.025 to 0.75 wt. % and in particular 0.05 to 0.5 wt. % of (sweet) almond oil, peach kernel oil, apricot kernel oil, avocado oil, soybean oil, sesame oil, sunflower oil, grape seed oil, amaranth seed oil, argan oil, olive oil, jojoba oil and/or mixtures of these oils.

For some application forms (e.g. for sensitive cleaning formulations) it can be advantageous if the cleaning agents according to the invention include a particularly gentle surfactant base. Cleaning agents according to the invention which in addition to the anionic surfactant a) preferably include 0.1 to 5 wt. %, preferably 0.2 to 4 wt. % and in particular 0.3 to 3 wt. % of at least one amphoteric, zwitterionic and/or non-ionic surfactant, the stated amounts relating to the total weight of the cleaning agent, include "a particularly gentle surfactant base".

Suitable amphoteric and/or zwitterionic surfactants can preferably be selected from one or more compounds of the following formulae (I) to (VII), in which the residue R denotes a straight-chain or branched, saturated or mono- or polyunsaturated alkyl or alkenyl residue having 7 to 23 carbon atoms (formulae (I) and (II)) or a straight-chain or branched, saturated or mono- or polyunsaturated alkyl or alkenyl residue having 8 to 24 carbon atoms (formulae (III) to (VII)):

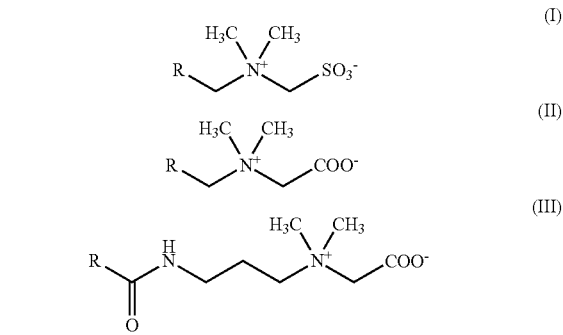

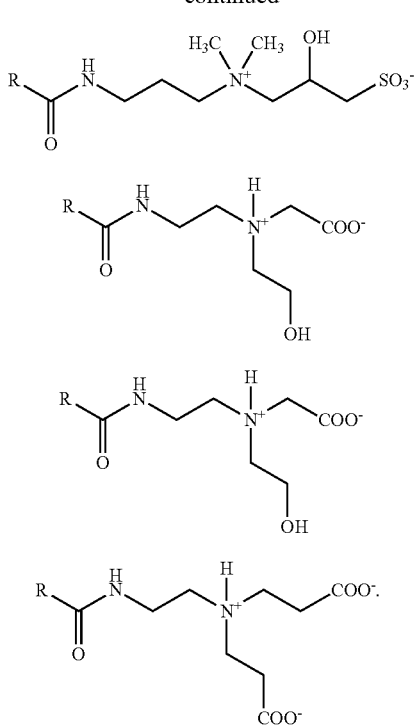

Preferred amphoteric and/or zwitterionic surfactants of one of the aforementioned formulae (I) to (VII) mostly include as the residue R a straight-chain or branched, saturated or mono- or polyunsaturated alkyl residue having 8 to 20, more preferably 8 to 16 and in particular 8 to 12 C atoms.

Amphoteric and/or zwitterionic surfactants in which the residue R is derived from coconut oil are more preferred.

The amphoteric/zwitterionic surfactants known under the INCI names Sodium Cocoamphoacetate, Disodium Cocoamphodiacetate, Sodium Cocoamphopropionate, Disodium Cocoamphodipropionate, Coco Betaine, Lauryl Betaine and/or Cocamidopropyl Betaine and commercially available from a number of suppliers are preferred in particular.

The suitable non-ionic surfactants/emulsifiers which can preferably be used in the cleaning agents according to the invention include for example:
- $C_8$-$C_{30}$ fatty acid monoesters and diesters of addition products of 1 to 30 mol of ethylene oxide with glycerol, amine oxides,
- addition products of 2 to 50 mol of ethylene oxide and/or 0 to 5 mol of propylene oxide with linear and branched fatty alcohols having 8 to 30 C atoms, with fatty acids having 8 to 30 C atoms and with alkyl phenols having 8 to 15 C atoms in the alkyl group,
- sorbitan fatty acid esters and addition products of ethylene oxide with sorbitan fatty acid esters such as for example polysorbates,
- fatty acid alkanolamides of the general formula (VIII),

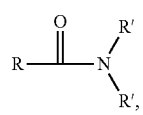

in which R preferably denotes a linear or branched, saturated or unsaturated alkyl or alkenyl residue having 8 to 24 carbon atoms and the residues R' denote hydrogen or the —(CH$_2$)$_n$OH group, in which n denotes the numbers 2 or 3, with the proviso that at least one of the residues R' denotes the aforementioned residue —(CH$_2$)$_n$OH, sugar fatty acid esters and addition products of ethylene oxide with sugar fatty acid esters,
- addition products of ethylene oxide with fatty acid alkanolamides and fatty amines, and/or
- alkyl polyglucosides.

Particularly preferred non-ionic surfactants which can be used in the cleaning agents according to the invention are fatty acid alkanolamides of the aforementioned formula (VIII). A fatty acid alkanolamide that is known under the INCI name Cocamide MEA and is commercially available from various suppliers is preferred in particular.

In a third preferred embodiment cleaning agents according to the invention include—relative in each case to their total weight—
a) 6 to 12 wt. %, preferably 7 to 11 wt. % and in particular 8 to 10 wt. % of at least one anionic surfactant,
b) 0.01 to 1 wt. %, preferably 0.025 to 0.75 wt. % and in particular 0.05 to 0.5 wt. % of at least one cationic guar polymer,
c) 0.05 to 2 wt. %, preferably 0.1 to 1.5 wt. % and in particular 0.2 to 1 wt. % of at least one silicone emulsion, which has an average silicone particle size by volume of a maximum of 600 nm,
d) 0.02 to 1 wt. %, preferably 0.03 to 0.75 wt. % and in particular 0.05 to 0.5 wt. % of at least one wax, and
e) 0.1 to 5 wt. %, preferably 0.2 to 4 wt. % and in particular 0.3 to 3 wt. % of at least one amphoteric, zwitterionic and/or non-ionic surfactant.

Within this embodiment it is particularly preferable if the cleaning agents according to the invention include—relative in each case to their total weight—
a) 6 to 12 wt. %, preferably 7 to 11 wt. % and in particular 8 to 10 wt. % of at least one alkyl sulfate and/or alkyl polyglycol ether sulfate salt of formula R—(OCH$_2$—CH$_2$)$_x$—OSO$_3^-$ X$^+$, in which R preferably denotes a linear or branched, saturated or unsaturated alkyl group having 8 to 30 C atoms, x denotes the number 0 or 1 to 12 and X denotes an alkali, alkaline-earth, ammonium or alkanolamine ion,
b) 0.01 to 1 wt. %, preferably 0.025 to 0.75 wt. % and in particular 0.05 to 0.5 wt. % of at least one cationic hydroxy($C_1$-$C_4$)alkyl guar derivative having an average molecular weight (weight-average) from 100,000 to 2,000,000 daltons, preferably from 400,000 to 1,750,000 daltons and in particular from 800,000 to 1,600,000 daltons,
c) 0.05 to 2 wt. %, preferably 0.1 to 1.5 wt. % and in particular 0.2 to 1 wt. % of at least one dimethyl polysiloxane emulsion, which has an average silicone particle size by volume of a maximum of 600 nm,
d) 0.02 to 1 wt. %, preferably 0.03 to 0.75 wt. % and in particular 0.05 to 0.5 wt. % of at least one wax of plant origin, which preferably has a melting point in the range from 80 to 90° C.,
e) 0.01 to 1 wt. %, preferably 0.025 to 0.75 wt. % and in particular 0.05 to 0.5 wt. % of at least one vegetable oil, and
f) 0.1 to 5 wt. %, preferably 0.2 to 4 wt. % and in particular 0.3 to 3 wt. % of at least one amphoteric, zwitterionic and/or non-ionic surfactant.

Cleaning agents that are preferred in particular within this third preferred embodiment include—relative to the total weight of the cleaning agents—
a) 6 to 12 wt. %, preferably 7 to 11 wt. % and in particular 8 to 10 wt. % of at least one straight-chain or branched alkyl ether sulfate of the above formula, which has an alkyl residue having 8 to 18 and in particular 10 to 16 C atoms and 1 to 6 and in particular 2 to 4 ethylene oxide units,
b) 0.01 to 1 wt. %, preferably 0.025 to 0.75 wt. % and in particular 0.05 to 0.5 wt. % of at least one cationic guar polymer known under the INCI name Guar Hydroxypropyltrimonium Chloride and having a molecular weight (weight-average) from 100,000 to 2,000,000 daltons, preferably from 400,000 to 1,750,000 daltons and in particular from 800,000 to 1,600,000 daltons and a cationic charge density of at least 0.5 meq/g,
c) 0.05 to 2 wt. %, preferably 0.1 to 1.5 wt. % and in particular 0.2 to 1 wt. % of at least one dimethyl polysiloxane emulsion, which has an average silicone particle size by volume of a maximum of 600 nm,
d) 0.02 to 1 wt. %, preferably 0.03 to 0.75 wt. % and in particular 0.05 to 0.5 wt. % of at least one hydrogenated vegetable oil, preferably hydrogenated castor oil,
e) 0.01 to 1 wt. %, preferably 0.025 to 0.75 wt. % and in particular 0.05 to 0.5 wt. % of (sweet) almond oil, peach kernel oil, apricot kernel oil, avocado oil, soybean oil, sesame oil, sunflower oil, grape seed oil, amaranth seed oil, argan oil, olive oil, jojoba oil and/or mixtures of these oils, and
f) 0.1 to 5 wt. %, preferably 0.2 to 4 wt. % and in particular 0.3 to 3 wt. % of at least one of the surfactants known under the INCI names Sodium Cocoamphoacetate, Disodium Cocoamphodiacetate, Sodium Cocoamphopropionate, Disodium Cocoamphodipropionate, Coco Betaine, Lauryl Betaine, Cocamidopropyl Betaine and/or Cocamide MEA.

In addition to the aforementioned ingredients, the cleaning agents according to the invention can also include a series of further optional active agents which impart advantageous properties thereto. These can be selected for example from:
further cationic polymers differing from b),
vitamins, vitamin derivatives and/or vitamin precursors,
further oils, fats and/or waxes differing from c) and/or d),
protein hydrolysates,
pearlescent agents,
plant extracts, and/or
anti-dandruff agents.

Particularly preferred further cationic polymers differing from b) are understood to be preferably quaternized cellulose derivatives.

Preferred quaternary cellulose derivatives are polymeric quaternary ammonium salts formed in the reaction of hydroxyethyl cellulose with trimethylammonium-substituted epoxides, for example the cationic polymers known under the INCI name Polyquarternium-10.

Polyquarternium-10 is commercially available from a number of suppliers.

The polymers known under the trade names Celquat®, Polymer JR® or Polymer LR® for example are suitable for the cleaning agents according to the invention.

Polymer JR® 400 from Amerchol is suitable in particular.

The further cationic polymer(s) differing from b) is (are) used in the cleaning agents according to the invention—relative to their total weight—in an amount preferably from 0.01 to 3 wt. %, more preferably from 0.02 to 2 wt. %, particularly preferably from 0.03 to 1.5 wt. % and in particular from 0.05 to 1 wt. %.

Suitable vitamins, vitamin derivatives and/or vitamin precursors can be included in the cleaning agents according to the invention—relative to the total weight of the cleaning agents—in an amount preferably from 0.001 to 5 wt. %, more preferably from 0.002 to 4 wt. % and particularly preferably from 0.0025 to 3 wt. %.

Suitable vitamins, provitamins and vitamin precursors are preferably vitamins, vitamin derivatives and vitamin precursors that are assigned to groups A, B, C, E, F and H. Vitamin A: The group of substances classed as vitamin A includes retinol (vitamin $A_1$) and 3,4-didehydroretinol (vitamin $A_2$). β-Carotene is the retinol provitamin. Suitable vitamin A components are for example vitamin A acid and esters thereof, vitamin A aldehyde and vitamin A alcohol and esters thereof such as the palmitate and acetate.
Vitamin B: The vitamin B group or vitamin B complex includes inter alia
Vitamin $B_1$ (thiamine)
Vitamin $B_2$ (riboflavin)
Vitamin $B_3$. The compounds nicotinic acid and nicotinic acid amide (niacinamide) are often included under this term.
Vitamin $B_5$ (pantothenic acid, panthenol and pantolactone). Within the context of this group panthenol and/or pantolactone is preferably used in the agents according to the invention. Derivatives of panthenol which can be used are in particular the esters and ethers of panthenol as well as cationically derivatized panthenols. Individual representatives are for example panthenol triacetate, panthenol monoethyl ether and the monoacetate thereof, and cationic panthenol derivatives.
Vitamin $B_6$ (pyridoxine as well as pyridoxamine and pyridoxal).
Vitamin C (ascorbic acid): Use in the form of the palmitic acid ester, glucosides or phosphates can be preferred. Use in combination with tocopherols can likewise be preferred.
Vitamin E (tocopherols, in particular α-tocopherol): These include tocopherol and derivatives thereof, which are understood in particular to be the esters such as the acetate, the nicotinate, the phosphate and the succinate.
Vitamin F: The term "vitamin F" is conventionally understood to mean essential fatty acids, in particular linoleic acid, linolenic acid and arachidonic acid.
Vitamin H: Vitamin H is the name given to the compound (3aS,4S,6aR)-2-oxohexahydrothienol[3,4-d]-imidazole-4-valeric acid, although this is now more widely known by the trivial name biotin.

Preferred cleaning agents according to the invention include at least one vitamin, vitamin derivative or vitamin precursor from the aforementioned groups A, B, E and H.

Particularly preferred cleaning agents according to the invention include at least one vitamin, vitamin derivative or vitamin precursor from the B group.

Cleaning agents according to the invention that are preferred in particular include niacinamide, panthenol, pantolactone and/or pyridoxine.

Further suitable oil, fat and/or wax components differing from c) and/or d) can be used in the cleaning agents according to the invention preferably in an amount from 0.001 to 10 wt. %, more preferably from 0.005 to 7.5 wt. % and in particular from 0.01 to 5 wt. %, the stated amounts relating to the total weight of the final cleaning agent.

They can be selected from natural, synthetic and/or mineral oil, fat and/or wax components.

Suitable mineral oils are in particular mineral oils, paraffin and isoparaffin oils and synthetic hydrocarbons. One example of a suitable hydrocarbon is the commercially available 1,3-di-(2-ethylhexyl)cyclohexane (Cetiol® S), for example.

A dialkyl ether can moreover serve as the oil component.

Suitable dialkyl ethers are in particular di-n-alkyl ethers having in total between 12 and 36 C atoms, in particular between 12 and 24 C atoms, such as for example di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether and n-hexyl-n-undecyl ether and also di-test-butyl ether, diisopentyl ether, di-3-ethyl decyl ether, tert-butyl-n-octyl ether, isopentyl-n-octyl ether and 2-methyl pentyl-n-octyl ether.

Di-n-octyl ether, which is commercially available under the name Cetiol® OE, is particularly preferred.

Fats are understood to be fatty acids, fatty alcohols and natural and synthetic waxes, which can be present both in solid form and in liquid form in aqueous dispersion.

Linear and/or branched, saturated and/or unsaturated fatty acids having 6 to 30 carbon atoms can be used as fatty acids. Fatty acids having 10 to 22 carbon atoms are preferred. Examples which can be cited include the isostearic acids, such as the commercial products Emersol® 871 and Emersol® 875, and isopalmitic acids such as the commercial product Edenor® IP 95, as well as all further fatty acids sold under the Edenor® trade names (Cognis). Further typical examples of such fatty acids are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, eicosanoic acid, gadoleic acid, docosanoic acid and erucic acid and technical mixtures thereof.

The fatty acid cuts obtainable from coconut oil or palm oil are conventionally particularly preferred; as a rule the use of stearic acid is preferred in particular.

Saturated, mono- or polyunsaturated, branched or unbranched fatty alcohols having $C_6$ to $C_{30}$, preferably $C_{10}$ to $C_{22}$ and most particularly preferably $C_{12}$ to $C_{22}$ carbon atoms can be used as fatty alcohols. For example, decanol, octanol, octenol, dodecenol, decenol, octadienol, decadienol, oleyl alcohol, erucic alcohol, ricinol alcohol, stearyl alcohol, isostearyl alcohol, cetyl alcohol, lauryl alcohol, myristyl alcohol, arachidyl alcohol, capryl alcohol, capric alcohol, linoleyl alcohol, linolenyl alcohol and behenyl alcohol, as well as the Guerbet alcohols thereof, can be used, wherein this list is intended to be of an exemplary and non-limiting nature. However, the fatty alcohols derive from preferably natural fatty acids, wherein it can conventionally be assumed that they are obtained from the esters of fatty acids by reduction. Fatty alcohol cuts which are produced by reduction of naturally occurring triglycerides such as beef fat, palm oil, groundnut oil, colza oil, cottonseed oil, soybean oil, sunflower oil and linseed oil or from fatty acid esters formed from the transesterification products thereof with corresponding alcohols and which thus represent a mixture of different fatty alcohols, can likewise be used. Such substances are available commercially for example under the names Stenol®, e.g. Stenol® 1618 or Lanette®, e.g. Lanette® O or Lorol®, e.g. Lorol® C8, Lorol® C14, Lorol® C18, Lorol® C8-18, HD-Ocenol®, Crodacol®, e.g. Crodacol® CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24.

Wool wax alcohols can of course also be used according to the invention, such as are available commercially for example under the names Corona®, White Swan®, Coronet® or Fluilan®.

Sunflower wax, fruit waxes, such as for example apple wax or citrus wax, and/or PE or PP microwaxes can be used as further natural or synthetic waxes differing from d). Such waxes are available for example via Kahl & Co., Trittau.

Further fats are, for example

- ester oils. Ester oils are understood to be the esters of $C_6$-$C_{30}$ fatty acids with $C_2$-$C_{30}$ fatty alcohols. The monoesters of fatty acids with alcohols having 2 to 24 C atoms are preferred. Examples of fatty acid components used in the esters are hexanoic acid, octanoic acid, 2-ethylhexanoic acid, decanoic acid, lauric acid, isotridecanoic acid, myristic acid, palmitic acid, palmitoleic acid, stearic acid, isostearic acid, oleic acid, elaidic acid, petroselic acid, linoleic acid, linolenic acid, elaeostearic acid, eicosanoic acid, gadoleic acid, docosanoic acid and erucic acid and technical mixtures thereof. Examples of the fatty alcohol components in the ester oils are isopropyl alcohol, hexanol, octanol, 2-ethylhexyl alcohol, decanol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof. Particularly preferred are isopropyl myristate (Rilanit® IPM), isononanoic acid $C_{16-18}$ alkyl ester (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinate/caprylate (Cetiol® LC), n-butyl stearate, oleyl erucate (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN), oleic acid decyl ester (Cetiol® V).
- dicarboxylic acid esters such as di-n-butyl adipate, di-(2-ethylhexyl) adipate, di-(2-ethylhexyl) succinate and diisotridecyl acelate and also diol esters such as ethylene glycol dioleate, ethylene glycol diisotridecanoate, propylene glycol di-(2-ethyl hexanoate), propylene glycol diisostearate, propylene glycol dipelargonate, butanediol diisostearate, neopentyl glycol dicaprylate,
- symmetrical, asymmetrical or cyclic esters of carbonic acid with fatty alcohols,
- glycerol carbonate or dicaprylyl carbonate (Cetiol® CC),
- ethoxylated or non-ethoxylated mono-, di- and tri-fatty acid esters of saturated and/or unsaturated linear and/or branched fatty acids with glycerol, such as for example Monomuls® 90-018, Monomuls® 90-L12, Cetiol® HE or Cutina® MD.

Suitable protein hydrolysates which can be used in the cleaning agents according to the invention are preferably of plant, animal or marine origin. They can be used in the agents according to the invention preferably in an amount from 0.01 to 10 wt. %, more preferably from 0.25 to 7.5 wt. % and in particular from 0.05 to 5 wt. %, the stated amounts relating to the total weight of the final cleaning agent.

Suitable animal protein hydrolysates are for example elastin, collagen, keratin, silk and/or milk protein hydrolysates, which can also be present in the form of salts.

Such products are sold for example under the trademarks Dehylan® (Cognis), Promois® (Interorgana), Collapuron®

(Cognis), Nutrilan® (Cognis), Gelita-Sol® (Deutsche Gelatine Fabriken Stoess & Co), Lexein® (Inolex) and Kerasol® (Croda).

Suitable protein hydrolysates of plant origin are for example soy, almond, rice, pea, potato, rapeseed and/or wheat protein hydrolysates.

Such products are available for example under the trademarks Gluadin® (Cognis), DiaMin® (Diamalt), Lexein® (Inolex) and Crotein® (Croda).

The suitable protein hydrolysates of marine origin include for example collagen hydrolysates of fish or algae and protein hydrolysates of mussels or pearl hydrolysates. Examples of suitable pearl hydrolysates are the commercial products Pearl Protein Extract BG® or Crodarom® Pearl.

Cationized protein hydrolysates can also be used, wherein the underlying protein hydrolysate can originate from the animal, plant and/or marine sources described above.

Cationic protein hydrolysates are moreover understood to include quaternized amino acids and mixtures thereof. The quaternization of protein hydrolysates or amino acids is frequently performed using quaternary ammonium salts such as for example N,N-dimethyl-N-(n-alkyl)-N-(2-hydroxy-3-chloro-n-propyl) ammonium halides.

The cationic protein hydrolysates can moreover also be further derivatized.

Typical examples of suitable cationic protein hydrolysates and/or derivatives are the commercially available products known under the following INCI names: Cocodimonium Hydroxypropyl Hydrolyzed Collagen, Cocodimonium Hydroxypropyl Hydrolyzed Casein, Cocodimonium Hydroxypropyl Hydrolyzed Collagen, Cocodimonium Hydroxypropyl Hydrolyzed Hair Keratin, Cocodimonium Hydroxypropyl Hydrolyzed Keratin, Cocodimonium Hydroxypropyl Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed Keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76 Hydrolyzed Collagen, Quaternium-79 Hydrolyzed Collagen, Quaternium-79 Hydrolyzed Keratin, Quaternium-79 Hydrolyzed Milk Protein, Quaternium-79 Hydrolyzed Silk, Quaternium-79 Hydrolyzed Soy Protein, Quaternium-79 Hydrolyzed Wheat Protein.

Suitable pearlescent agents according to the invention are for example
glycol distearic acid esters,
$C_8$-$C_{30}$ fatty acid monoglycol esters and/or
mica pigments coated with titanium dioxide,
such as are available for example under the trade names Rewopal®, Genapol® PMS, Cutina® EGMS, Timiron®, Colorona® and Euperlan®.

The pearlescent agent(s) can be used in the cleaning agents according to the invention—relative to their weight—preferably in amounts from 0.01 to 3 wt. %, more preferably from 0.025 to 2 wt. % and particularly preferably from 0.05 to 1 wt. %.

Suitable plant extracts are understood to be extracts which can be produced from all parts of a plant.

These extracts are conventionally produced by extraction of the entire plant. It can also be preferable in individual cases, however, to produce the extracts exclusively from flowers and/or leaves of the plant.

The extracts from green tea, oak bark, stinging nettle, witch hazel, hops, chamomile, burdock, horsetail, whitethorn, lime blossom, lychee, almond, aloe vera, pine, horse chestnut, sandalwood, juniper, coconut, mango, apricot, lemon, wheat, kiwi, melon, orange, grapefruit, sage, rosemary, birch, mallow, lady's smock, wild thyme, yarrow, thyme, *melissa*, restharrow, coltsfoot, marshmallow, *ginseng*, ginger root, *Echinacea purpurea, Olea europaea, Foeniculum vulgaris* and *Apium graveolens* are preferred above all according to the invention.

Water, alcohols and mixtures thereof can be used as extracting agents to produce the cited plant extracts. Of the alcohols, low alcohols such as ethanol and isopropanol, but in particular polyhydric alcohols such as ethylene glycol and propylene glycol, are preferred, both as the sole extracting agent and mixed with water. Plant extracts based on water/propylene glycol in the ratio 1:10 to 10:1 have proved to be particularly suitable.

The plant extracts can be used according to the invention in both pure and diluted form. If they are used in diluted form they conventionally include approximately 2 to 80 wt. % of active substance and as the solvent the extracting agent or mixture of extracting agents used to obtain them.

The plant extract(s) can be included in the cleaning agents according to the invention preferably in an amount from 0.001 to 5 wt. %, more preferably from 0.002 to 3 wt. % and in particular from 0.005 to 2 wt. %, the stated amounts relating to the total weight of the cosmetic cleaning agents.

Anti-dandruff active agents can be used in the cosmetic cleaning agents according to the invention (relative to the total weight of the cleaning agents) preferably in an amount from 0.025 to 7.5 wt. %, particularly preferably from 0.05 to 5 wt. % and in particular from 0.075 to 3 wt. %.

Suitable anti-dandruff active agents can be selected from piroctone olamine, climbazole, zinc pyrithione, ketoconazoles, salicylic acid, sulfur, selenium sulfide, tar preparations, undecenoic acid derivatives, burdock extracts, poplar extracts, stinging nettle extracts, walnut shell extracts, birch extracts, willow bark extracts, rosemary extracts and/or *arnica* extracts.

Climbazole, zinc pyrithione and piroctone olamine are preferred, with zinc pyrithione being preferred in particular.

Preferred embodiments of the cosmetic cleaning agents according to the invention are hair shampoos, shower washes, shower gels, hair rinses, hair masks, aftershaves and/or deodorants. Cleaning agents according to the invention which serve to clean the hair and scalp are preferred in particular.

Cleaning agents according to the invention preferably have a pH in the range from 4 to 5.7, more preferably from 4.2 to 5.5 and in particular from 4.5 to 5.3.

In addition to the required and preferred components, the cleaning preparations according to the invention can include further components known to the person skilled in the art for such cosmetic agents.

These include for example:
texturizing agents such as maleic acid and lactic acid,
active agents to improve the fiber structure, in particular mono-, di- and oligosaccharides such as for example glucose, galactose, fructose, fruit sugar and lactose,
dyes to color the agent,
further substances to adjust the pH, such as for example α- and β-hydroxycarboxylic acids,
active agents such as allantoin and bisabolol,
complexing agents such as EDTA, NTA, β-alanine diacetic acid and phosphonic acids,
propellants such as propane-butane mixtures, $N_2O$, dimethyl ether, $CO_2$ and air,
consistency modifiers such as sugar esters, polyol esters or polyol alkyl ethers,
preservatives, such as for example sodium benzoate or salicylic acid,
viscosity adjusters such as salts (NaCl).

The cleaning agents according to the invention have outstanding properties.

They are stable and in combination with water form a rich foam which is easily distributed on the application surface.

They include lower amounts of various care components (cationic polymers, silicones, oils) and/or lower amounts of surfactants than commercial shampoos, yet they have a comparable care performance. Resources are thus used more efficiently in the production of the cleaning agents according to the invention.

Hair treated with the agents according to the invention has in particular an improved combability, an improved feel and an improved shine.

EXAMPLES

The following table includes examples of cleaning compositions according to the invention (example 2) and of comparative compositions (examples 1 and 3). Unless otherwise specified, the stated amounts in the table relate to percentages by weight.

|  | 1 | 2 | 3 |
|---|---|---|---|
| Sodium laureth sulfate (2EO) | 10.80 | 9.00 | 7.00 |
| Sodium lauryl sulfate |  |  | 5.00 |
| Disodium cocoamphodiacetate | 3.20 | 0.80 |  |
| Cocamidopropyl betaine |  | 1.60 |  |
| Ammonium xylene sulfonate |  |  | 1.00 |
| Cocamide MEA |  | 0.45 | 0.60 |
| PEG-7 glyceryl cocoate | 1.20 | 0.40 | 0.40 |
| PEG-40 hydrogenated castor oil |  | 0.30 | 0.30 |
| PEG-55 propylene glycol oleate | 0.40 |  |  |
| Laureth-2 | 0.40 |  |  |
| Polymer JR ®[1] 400 | 0.70 |  | 0.30 |
| Guar hydroxypropyl trimonium chloride |  | 0.30 |  |
| PEG-12 dimethicone | 1.00 |  |  |
| Xiameter ®[2] MEM 1664 Emulsion |  | 0.40 | 1.20 |
| Almond oil, sweet |  | 0.05 |  |

-continued

|  | 1 | 2 | 3 |
|---|---|---|---|
| Hydrogenated castor oil | 0.20 | 0.10 | 0.10 |
| Pearlescent agent | 0.10 | 0.10 | 0.10 |
| Electrolyte (e.g. NaCl to adjust the viscosity to 8000 to 9000 mPas*) | 0.60 | 1.20 | 1.10 |
| Acidulants, preservatives, perfume | qs | qs | qs |
| Water | to 100 | to 100 | to 100 |
| Total active agent content (surfactants and oils/waxes) | 17.90 | 13.40 | 17.10 |
| Average rating | 5.8 | 5.9 | 5.9 |
| Reduction in wet combability | 62 | 65 | 54 |
| Reduction in dry combability | −28 | 51 | 25 |

*The viscosity in each case was determined using a Haake VT550 rotary viscometer at a temperature of 20° C.; measuring device MV; spindle MV II, 8 rpm.

The following commercial products were used in the examples above:

1 INCI name: Polyquaternium-10; Dow

2 INCI name: Dimethicone, Laureth-4, Laureth-23; Dow Corning

The aforementioned shampoos were rated as follows:

Around 200 independent testers aged from 20 to 60 (50% aged from 20 to 40 and 50% aged from 41 to 60) used the coded shampoos in a blind test (interviewer-assisted home use test).

They then rated the shampoos on a scale from 1 to 7, where "7" denotes very satisfied, "6" satisfied, "5" would use, "4" OK, "3" not so good, "2" poor and "1" very poor.

The reduction in wet and dry combability was determined using the conventional method (WO 2004/26270A1), by comparing the reduction in combing force for a bleached hair strand washed with the corresponding shampoo (wet and dry) with that for an untreated hair strand washed with the corresponding shampoo (wet and dry).

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method of improving the dry combability of hair strands, including:
cleaning the hair strands with a cosmetic cleaning agent including—relative to its total weight—
a) 6 to 12 wt. % of at least one anionic surfactant,
b) 0.01 to 1 wt. % of at least one cationic guar polymer known under the INCI name Guar Hydroxypropyltrimonium Chloride and having a molecular weight (weight-average) from 100,000 to 2,000,000 daltons and a cationic charge density of at least 0.5 meq/g,
c) 0.05 to 2 wt. % of at least one dimethyl polysiloxane emulsion, which has an average silicone particle size by volume of a maximum of 600 nm and viscosity at a temperature of 25° C. of 30,000 to 100,000 cSt, wherein the at least one dimethyl polysiloxane emulsion comprises
- (i) 20 to 80 wt. % of at least one polydialkyl siloxane, and
- (ii) at least two different non-ionic emulsifiers, which are selected from in each case from the group consisting of 1- to 5-times alkoxylated C8-C24 alcohols and 18- to 30-times alkoxylated C8-C24 alcohols, the stated amounts relating to the weight of the emulsion,
- d) 0.02 to 1 wt. % of at least one hydrogenated vegetable oil, and
- e) 0.01 to 1 wt. % of (sweet) almond oil, peach kernel oil, apricot kernel oil, avocado oil, soybean oil, sesame oil, sunflower oil, grape seed oil, amaranth seed oil, argan oil, olive oil, jojoba oil and/or mixtures of these oils, wherein the total concentration of all combined surfactants and oils and waxes is about 13 wt. % or less, and drying and then combing the hair strands after rinsing the cosmetic cleaning agent from the hair strands, wherein the dried hair strands require reduced combing force after performing the cleaning, rinsing, and drying steps than before performing such steps.

2. The method according to claim 1, wherein the at least one anionic surfactant is selected from the group consisting of alkyl sulfate and/or alkyl polyglycol ether sulfate salts of formula R—(OCH$_2$—CH$_2$)$_x$—OSO$_3$ X, in which R denotes a linear or branched, saturated or unsaturated alkyl group having 8 to 30 C atoms, x denotes 0 or a number from 1 to 12 and X denotes an alkali, an alkaline-earth, an ammonium or an alkanolamine ion.

3. The method according to claim 1, wherein the at least one hydrogenated vegetable oil d) has a melting point in the range from 80 to 90° C.

4. The method according to claim 1, further comprising—relative to its total weight—0.1 to 5 wt. % of at least one amphoteric, zwitterionic and/or non-ionic surfactant.

5. The method according to claim 4, wherein at least one of the surfactants included in the agent is known under the INCI names Sodium Cocoamphoacetate, Disodium Cocoamphodiacetate, Sodium Cocoamphopropionate, Disodium Cocoamphodipropionate, Coco Betaine, Lauryl Betaine, Cocamidopropyl Betaine and Cocamide MEA.

6. The method according to claim 1, further comprising—relative to its total weight—0.025 to 7.5 wt. % of at least one anti-dandruff active agent.

7. The method according to claim 1, wherein the agent has a pH in the range from 4 to 5.7.

8. The method according to claim 1, wherein at least two different non-ionic emulsifiers are ethoxylated lauryl alcohols and the at least one hydrogenated vegetable oil includes castor oil.

9. The method according to claim 1, wherein at least two different non-ionic emulsifiers are known under the INCI names Laureth-4 and Laureth-23, and the at least one hydrogenated vegetable oil includes castor oil.

* * * * *